United States Patent
Flanders

(10) Patent No.: US 9,717,422 B2
(45) Date of Patent: Aug. 1, 2017

(54) SHEATH WITH OPTICALLY INTERROGATABLE SENSORS

(71) Applicant: Volcano Corporation, San Diego, CA (US)

(72) Inventor: Dale C. Flanders, Lexington, MA (US)

(73) Assignee: VOLCANO CORPORATION, San Diego, CA (US)

( * ) Notice: Subject to any disclaimer, the term of this patent is extended or adjusted under 35 U.S.C. 154(b) by 1007 days.

(21) Appl. No.: 13/712,368

(22) Filed: Dec. 12, 2012

(65) Prior Publication Data

US 2014/0163392 A1    Jun. 12, 2014

(51) Int. Cl.
*A61B 5/02* (2006.01)
*A61B 5/0215* (2006.01)
*A61B 5/01* (2006.01)
*A61B 5/00* (2006.01)
*A61B 1/04* (2006.01)

(52) U.S. Cl.
CPC ............ *A61B 5/02154* (2013.01); *A61B 1/04* (2013.01); *A61B 5/01* (2013.01); *A61B 5/02158* (2013.01); *A61B 5/6852* (2013.01); *A61B 5/0002* (2013.01); *A61B 5/0066* (2013.01); *A61B 5/0084* (2013.01); *A61B 5/02156* (2013.01); *A61B 2562/0247* (2013.01); *A61B 2562/0271* (2013.01); *A61B 2562/043* (2013.01); *A61B 2562/12* (2013.01); *A61B 2562/164* (2013.01)

(58) Field of Classification Search
CPC .................................................. A61B 5/02154
See application file for complete search history.

(56) References Cited

U.S. PATENT DOCUMENTS

| | | | |
|---|---|---|---|
| 4,691,708 A | 9/1987 | Kane | |
| 4,730,622 A | 3/1988 | Cohen | |
| 5,394,488 A | 2/1995 | Fernald et al. | |
| 6,125,216 A | 9/2000 | Haran et al. | |
| 6,134,003 A | 10/2000 | Tearney et al. | |
| 6,203,493 B1 * | 3/2001 | Ben-Haim | ......... A61B 1/00135 600/117 |

(Continued)

FOREIGN PATENT DOCUMENTS

| | | | | |
|---|---|---|---|---|
| NZ | WO 2004026127 A1 * | 4/2004 | .......... A61B 5/0215 |
| WO | 9001294 A1 | 7/1989 | |

(Continued)

OTHER PUBLICATIONS

Huber, R., et al., "Fourier Domain Mode Locking (FDML): A new laser operating regime and applications for optical coherence tomography," Optics Express, vol. 14, No. 8, Apr. 17, 2006, pp. 3225-3237.

(Continued)

*Primary Examiner* — Joseph M Santos Rodriguez

(57) ABSTRACT

An intravascular sensor system including an array of pressure and/or temperature sensors for detecting pressure and/or temperature. In one example, the sensors are interrogated with an optical catheter. In this example, the swept source is able to acquire both image and pressure/temperature data of a patient's vessel or artery. In another example, the intravascular pressure sensor system has a sheath embedded with pressure sensors in the sheath wall. Other examples include the process of making and using the intravascular pressure sensor system.

17 Claims, 13 Drawing Sheets

(56) References Cited

U.S. PATENT DOCUMENTS

| | | | |
|---|---|---|---|
| 6,278,811 B1 | 8/2001 | Hay et al. | |
| 6,665,458 B2 | 12/2003 | Korn | |
| 6,740,866 B1 | 5/2004 | Bohnert et al. | |
| 7,011,647 B2 | 3/2006 | Purdy et al. | |
| 7,061,618 B2 | 6/2006 | Atia et al. | |
| 7,129,470 B2 | 10/2006 | MacDougall | |
| 7,196,318 B2 | 3/2007 | Shin et al. | |
| 7,215,416 B2 | 5/2007 | Yamate et al. | |
| 7,305,888 B2 * | 12/2007 | Walchli | G01L 9/0079 73/714 |
| 7,415,049 B2 | 8/2008 | Flanders et al. | |
| 7,421,905 B2 | 9/2008 | Zerwekh et al. | |
| 7,481,771 B2 | 1/2009 | Fonseca et al. | |
| 7,532,920 B1 | 5/2009 | Ainsworth et al. | |
| 7,646,946 B2 | 1/2010 | Lagakos et al. | |
| 7,775,966 B2 | 8/2010 | Dlugos et al. | |
| 7,776,380 B2 | 8/2010 | Pursley | |
| 7,778,500 B2 | 8/2010 | Ng et al. | |
| 7,931,597 B2 | 4/2011 | Bodecker et al. | |
| 7,931,598 B2 | 4/2011 | Bodecker et al. | |
| 8,016,814 B2 | 9/2011 | Blakstvedt et al. | |
| 8,050,523 B2 | 11/2011 | Younge et al. | |
| 8,208,990 B2 | 6/2012 | Maschke | |
| 2002/0028034 A1 | 3/2002 | Chen et al. | |
| 2004/0082867 A1 | 4/2004 | Esch et al. | |
| 2004/0263857 A1 | 12/2004 | Basavanhally et al. | |
| 2006/0011820 A1 | 1/2006 | Chow-Shing et al. | |
| 2006/0030753 A1 * | 2/2006 | Boutillette | A61B 1/00071 600/146 |
| 2007/0066890 A1 | 3/2007 | Maschke | |
| 2008/0039728 A1 * | 2/2008 | Pal | A61B 8/12 600/471 |
| 2008/0177183 A1 | 7/2008 | Courtney et al. | |
| 2009/0092352 A1 | 4/2009 | Ng et al. | |
| 2010/0220334 A1 | 9/2010 | Condit et al. | |
| 2011/0004075 A1 | 1/2011 | Stahmann et al. | |
| 2011/0051143 A1 | 3/2011 | Flanders et al. | |
| 2011/0051148 A1 | 3/2011 | Flanders et al. | |
| 2011/0092955 A1 * | 4/2011 | Purdy | A61B 5/0215 604/523 |
| 2011/0178413 A1 | 7/2011 | Schmitt et al. | |
| 2011/0182550 A1 | 7/2011 | Flanders et al. | |
| 2012/0162662 A1 | 6/2012 | Johnson et al. | |
| 2012/0220883 A1 | 8/2012 | Manstrom et al. | |
| 2013/0317372 A1 * | 11/2013 | Eberle | G01L 1/246 600/478 |

FOREIGN PATENT DOCUMENTS

| | | |
|---|---|---|
| WO | 2011034491 A1 | 3/2011 |
| WO | 2011091408 A2 | 7/2011 |

OTHER PUBLICATIONS

International Search Report and Written Opinion of the International Searching Authority mailed Mar. 12, 2014 from counterpart International Application No. PCT/US2013/073968, filed Dec. 10, 2013.

Bromley, E.I., et al, "A technique for the determination of stress in thin films," J. Vac. Sci. Technol. B 1 (4), Oct.-Dec. 1983, © American Vacuum society, pp. 1364-1366.

* cited by examiner

SHEATH WITH OPTICALLY INTERROGATABLE SENSORS

BACKGROUND OF THE INVENTION

Heart disease is a leading cause of death for men and women in the United States. Consequently, there are numerous medications, medical procedures, and medical devices for diagnosing and treating heart disease.

One type of medical procedure aimed at diagnosing heart disease is angiography. The procedure requires injecting a contrast agent into the blood stream and then taking x-ray images to determine if there is a blockage within the blood vessel.

A problem with an angiography is that the procedure can only determine if a blockage exists, but not whether the blockage is actually affecting the blood flow within the blood vessel. As a result, many patients elect to have unnecessary procedures to treat the blockage without confirming the severity of the blockage.

Another procedure for assessing heart disease is fractional flow reserve (FFR). FFR is a technique used in coronary catheterization to measure the pressure difference and thus blood flow across a partially blocked or constricted artery. Using a guidewire system, measurements are taken on both sides of a blockage within a blood vessel to determine if there is a pressure gradient or reduced blood flow due to the blockage. If there is no drop in pressure (or a nominal drop), then there may be no need for further medical intervention because the blockage is not significantly impeding the flow of blood. Conversely, if there is a significant drop across the blockage, then the blockage may need to be removed or treated because the blood flow is impaired by the blockage.

Generally, the FFR procedure is performed by inserting a guidewire system into the femoral or radial artery of the patient. The guidewire is maneuvered into position within a partially blocked blood vessel, and a sensor at the distal end of the guidewire is used to measure pressure, temperature, and/or blood flow to determine the severity of the blockage. The sensor is connected to a display device such as a monitor of a computer screen to display the patient's readings during the procedure.

Swept source catheters are also useful for assessing heart disease. For example, with OCT catheters, a section of a patient's vessel is scanned to accumulate linear or two dimensional image data which are used to build up a volumetric image of the blood vessel. One specific application involves the scanning of arteries, such as coronary arteries. The OCT catheter is inserted into an artery segment of interest typically using a guidewire system. The OCT catheter is then rotated and drawn back through the artery to produce a helical scan of the inner vessel wall. In a similar technology, a swept source catheter is used to determine the spectral response and thus the chemical constituents of the vessels walls, but typically not volumetric vessel images.

SUMMARY OF THE INVENTION

The present invention concerns the use of an array of pressure sensors to detect pressure within an intravascular system. One embodiment of this invention includes an intravascular pressure sensor system integrating the array of pressure sensors with a swept source catheter. In this embodiment, the swept source is able to acquire both image and pressure data of a patient's vessel or artery for example. In addition, the system is able to acquire a pressure profile along the length of an artery/vessel.

In general, according to one aspect, the invention features an intravascular pressure sensor system including an intravascular sensor array and a swept source catheter. The intravascular sensor array is inserted into a vessel of a patient. The swept source catheter is inserted along the length of the sensor array and optically interrogates the sensor array.

In general, according to another aspect, the invention features an intravascular pressure sensor system having a sheath and a number of pressure sensors. The sheath is inserted into a vessel of a patient. The pressure sensors are embedded within or on a wall of the sheath.

In general, according to another aspect, the invention features a method of making an intravascular pressure sensor device. This method includes spraying a first coat of a polymer on a mandrel. Then, placing pressure sensors on the first coat. Then, spraying a second coat of polymer over the pressure sensors. An intravascular sheath product with the embedded pressure sensors is removed from the mandrel.

In general, according to still another aspect, the invention features a method of detecting an intravascular pressure. This method includes inserting an intravascular sheath embedded with pressure sensors into a vessel of a patient. Then, inserting a swept source catheter into the sheath. Then, the vessel is scanned with a swept source optical signal from the swept source catheter. The swept source catheter is drawn through the sheath. Then, the pressure sensors are scanned with the swept source optical signal. The pressures are determined based on optical responses of the pressure sensors to the swept source optical signal.

In general, according to still another aspect, the invention features a method of calibrating a pressure sensor array system. This method includes placing a pressure sensor array system with embedded pressure sensors in a pressure vessel. Then, the pressure vessel is set to a first pressure. Then, the pressure sensors are optically interrogated. Then, the pressure vessel is set to a next pressure. The pressure sensors are optically interrogated again. This method results in the generation of a calibration table of wavelength changes as a function of pressure change for each of the pressure sensors.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same or similar parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
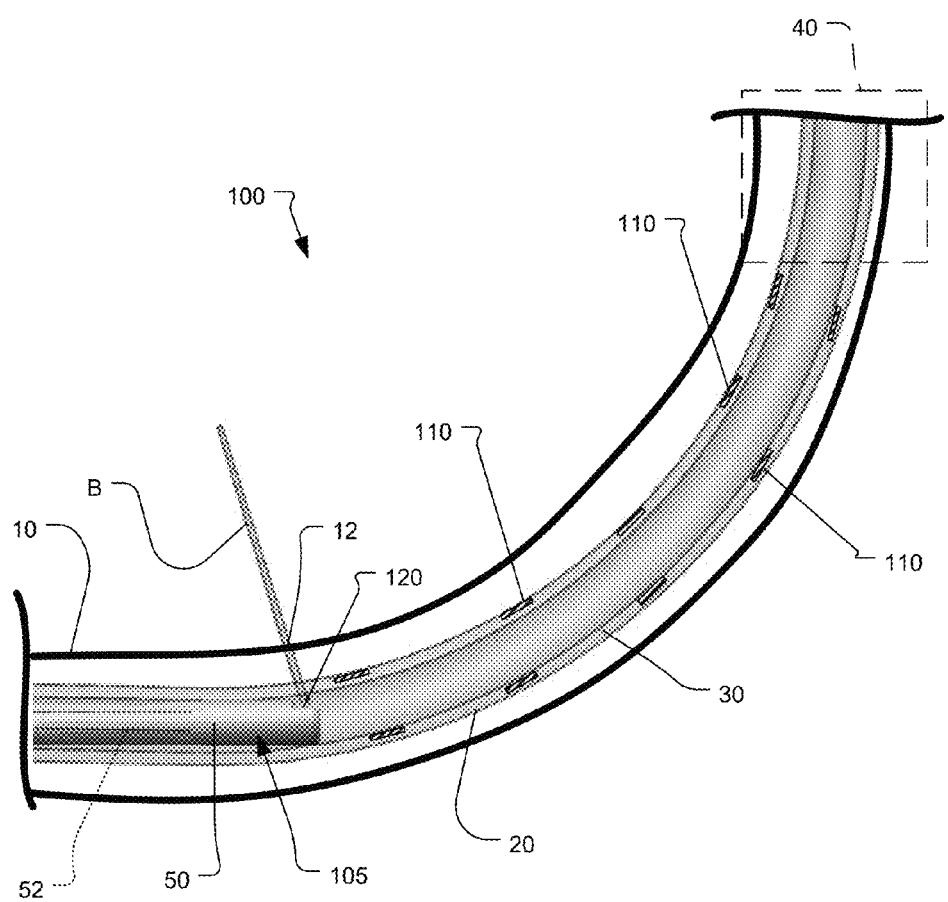
FIG. 1 is a cross-sectional view of an intravascular pressure sensor system in the lumen of a patient according to an embodiment of the invention.
Figure 2:
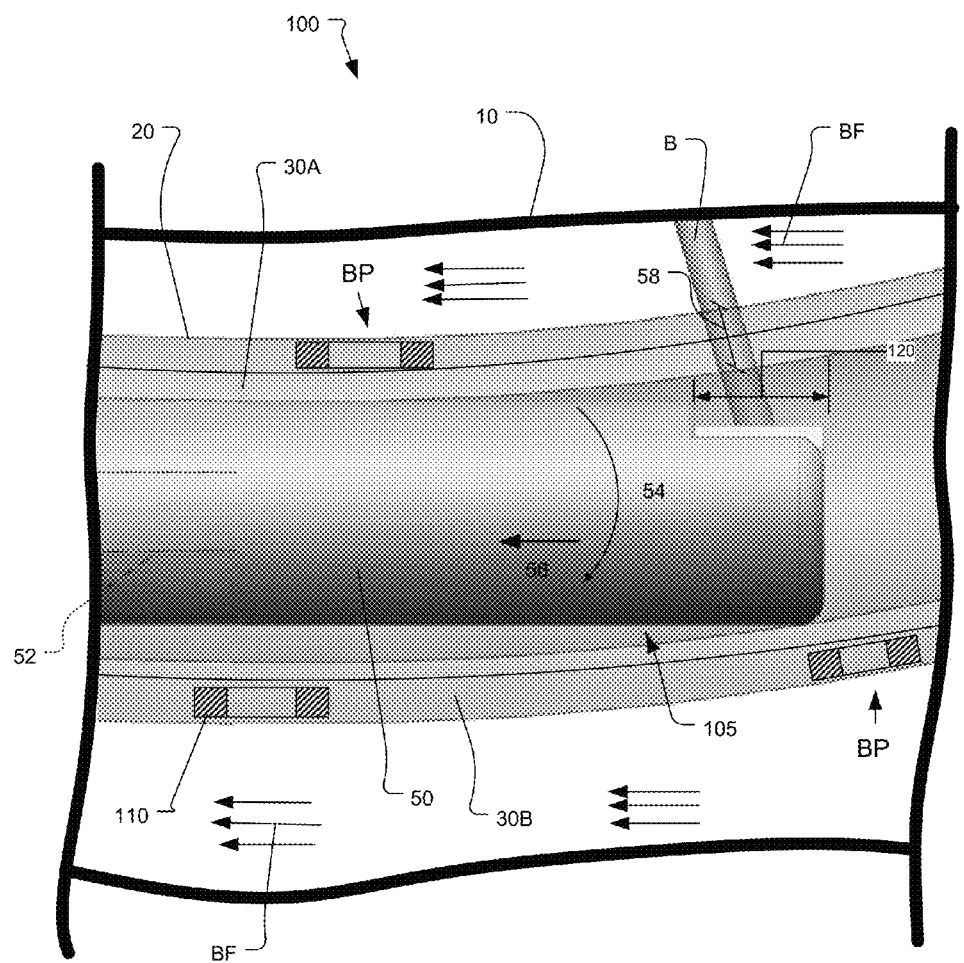
FIG. 2 is a detailed view of the swept source catheter from FIG. 1 in a sheath of the pressure sensor system.

FIGS. 1 and 2 illustrate an intravascular sensor system 100 to which the present invention is applicable.

The intravascular sensor system 100 is shown within a lumen 10 of a human body. In one example, the lumen 10 is a blood vessel, such as a coronary or carotid artery.

The intravascular sensor system 100 includes a catheter 50, such as a swept source catheter. The swept source catheter 50 includes a probe 105 located at the end of the catheter 50. The probe 105 emits and receives an optical beam B in a direction that is lateral to the probe 105.

The swept source catheter 50 also includes an optical fiber 52 extending longitudinally in the catheter 50. This optical fiber 52 transmits beam B to and from the probe 105.

The intravascular sensor system 100 includes a sheath 20. The sheath 20 is inserted into the lumen/vessel 10 of a body. The swept source catheter 50 is inserted and guided into the sheath 20. In one example, the sheath 20 is tubular, optically transmissive, and functions to protect the lumen/vessel 10 from catheter movement.

The sheath 20 has a wall 30 embedded with an array of sensors 110 along the length of the sheath 20. In one embodiment, the sensors 110 are pressure sensors. In other examples, the sensors 110 are temperature sensors. In still other embodiments, the sensors 110 are a combination of pressure sensors and temperature sensors.

In a preferred embodiment, the sensors 110 include pressure sensors. These pressure sensors 110 are used to detect the pressure in multiple locations along the length of the lumen/vessel 10. In use, the beam B from the swept source catheter 50 scans and optically interrogates the pressure sensors 110. The swept source catheter 50 is able to spectral response data from these pressure sensors 110 during scanning.

The sheath 20 includes an imaging region 40 where the swept source catheter 50 collects image data from the lumen/vessel 10. This imaging region 40 of the sheath 20 is free from embedded pressure sensors 110, in a currently preferred embodiment.

In more detail, the sheath 20 is inserted into the lumen/vessel 10. The swept source catheter 50 is introduced within the sheath 20. The beam B is emitted and collected through an optical port 120 of the probe 105. In the example of an OCT probe, the beam B is used to analyze the refractive index profile (A-scan) in the illuminated region 12 of the lumen/vessel 10. The beam B is also used to optically interrogate the pressure sensors 110 embedded along the sheath 20. A complete scan of the inner wall of the lumen/vessel 10 is collected by helically scanning the probe 105 along a segment of the lumen/vessel 10 marked as the imaging region 40.

FIG. 2 illustrates a more detailed view of the intravascular pressure sensor system 100 in operation. The beam B is transmitted through the optical port 120 of the swept source catheter 50 and then through the sheath wall 30, see reference 58. The beam B scans the lumen/vessel 10 as well as the pressure sensors 110. This is typically achieved by simultaneously rotating the probe 105, see arrow 54, while simultaneously withdrawing the probe 105 through the segment of interest, see arrow 56. The sheath 20 protects the lumen/vessel 10 during these scanning operations.

As described above, the sheath wall 30 is embedded with pressure sensors 110. The sheath wall 30 includes an inner wall section 30A and an outer wall section 30B. In this example, these wall sections 30A, 30B are formed with layers of polymer. The pressure sensors 110 are embedded particularly within the outer wall section 30B in this example.

FIG. 2 also illustrates the interaction of the blood flow BF with the embedded pressure sensors 110. The flowing blood BF has a blood pressure BP that can vary at different positions along the length of the lumen/vessel 10. The varied blood pressures BP are sensed by the pressure sensors 110 along the length of the sheath 20. As the blood flow BF passes by the pressure sensors, it exerts a blood pressure BP that is detected mechanically by the pressure sensor.

Figure 3:
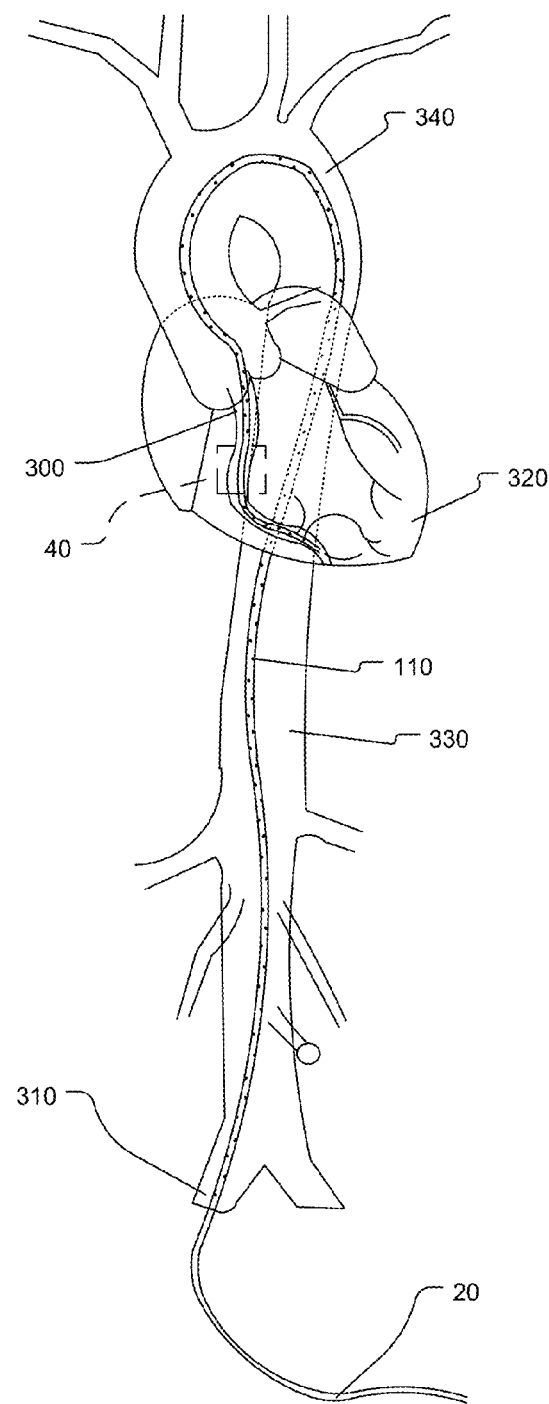
FIG. 3 is a schematic view of the human circulatory system with the sheath extending from the femoral artery to the coronary artery of a patient's heart according to an embodiment of the invention.

FIG. 3 shows the sheath 20 embedded with pressure sensors 110 within the human circulatory system. The sheath 20 extends to the coronary artery 300 inside the heart 320, according to one application. The sheath 20 is initially inserted into the femoral artery 310 in the leg of a patient. From the femoral artery 310, the sheath 20 is extended to the thoracic aorta 330. The sheath 20 is directed from the thoracic aorta 330 along the aortic arch 340 to the coronary artery 300 in the heart 320. In one example, the sheath has a length of about 1.5 meters, long enough to stretch from the femoral artery 310 to the coronary artery 300. In alternative embodiments, the sheath 20 is inserted via the radial or other artery, or vein. In other applications, other arteries or veins are the vessels of interest.

Figure 4:
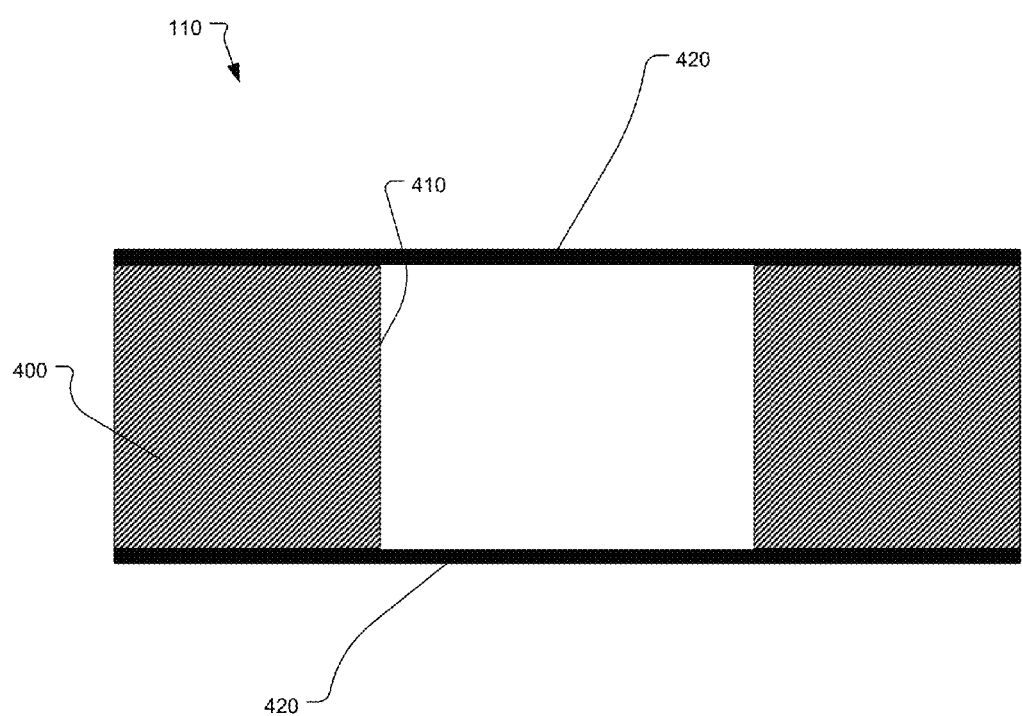
FIG. 4 is a cross-sectional view of the pressure sensor according to an embodiment of the invention.

FIG. 4 shows a detailed view of the pressure sensor 110. The pressure sensor 110 includes a substrate 400 that is the base of the sensor 110. In this example, the substrate 400 has a hollow cylindrical shape with a diameter of preferably less than 1 millimeter (mm) and a thickness of less than 0.5 mm. A port 410 extends through the center of the substrate 400. In one example, the substrate 400 is made from a wafer material such as a silicon wafer.

The pressure sensor 110 further includes a set of membranes 420 or diaphragms. A first membrane 420 is attached or fabricated on the substrate 400 so that it extends over one end of the port 410. A second membrane 420 is attached or fabricated to an opposite side of the substrate 400 extending over the other end of the port 410. The membrane 420 can be made from silicon nitride or silicon wafer material, for example.

The pressure sensor 110 is manufactured with an internal manufacturing pressure in the port 410. This manufacturing pressure is typically equal to the manufacturing ambient pressure, for example. The manufacturing ambient pressure is usually based on the conditions within a tool used to manufacture the sensors 110. More particularly, the internal manufacturing pressure is based on the temperature and quantity of gas sealed within the port 410 of the pressure sensor 110.

As described above, these pressure sensors 110 can be used within the human body. In one example, the sensors 110 are manufactured to take into account the human body temperature and pressure. The temperature within the human body is about 37 degrees Celsius. Therefore, this temperature along with the pressure of the blood can cause the membranes 420 to flex inwards if they are manufactured at room temperature and pressure. In one embodiment, the pressure sensors 110 are manufactured at higher temperature or pressure. When the pressure sensors are inserted into a patient, the membranes 420 flex to a neutral or flat position.

Figure 5A:
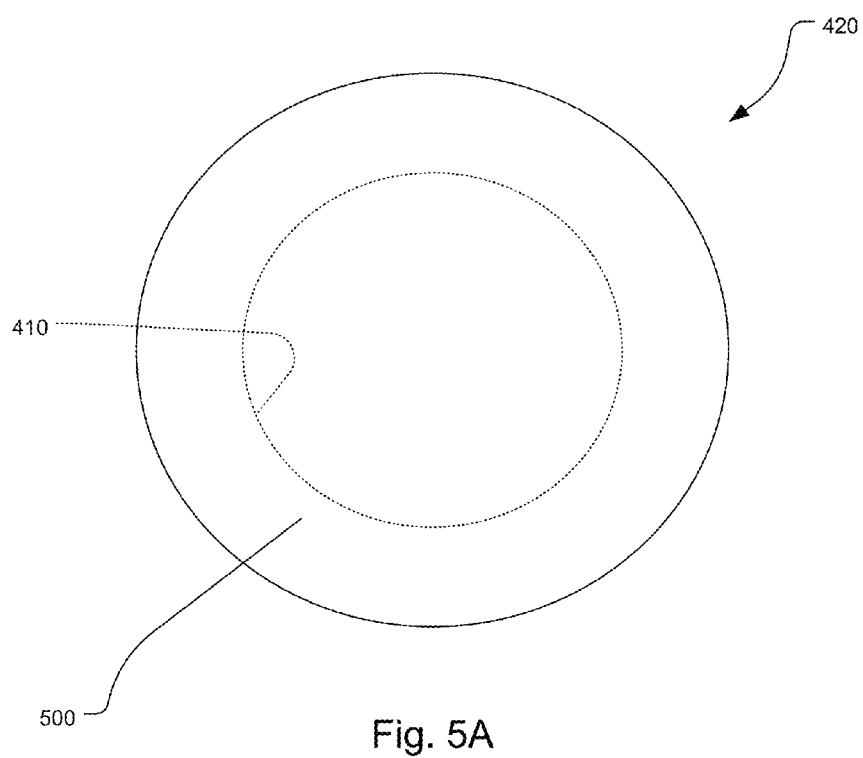
FIG. 5A is top view of a membrane from the pressure sensor according to an embodiment of the invention.
Figure 5B:
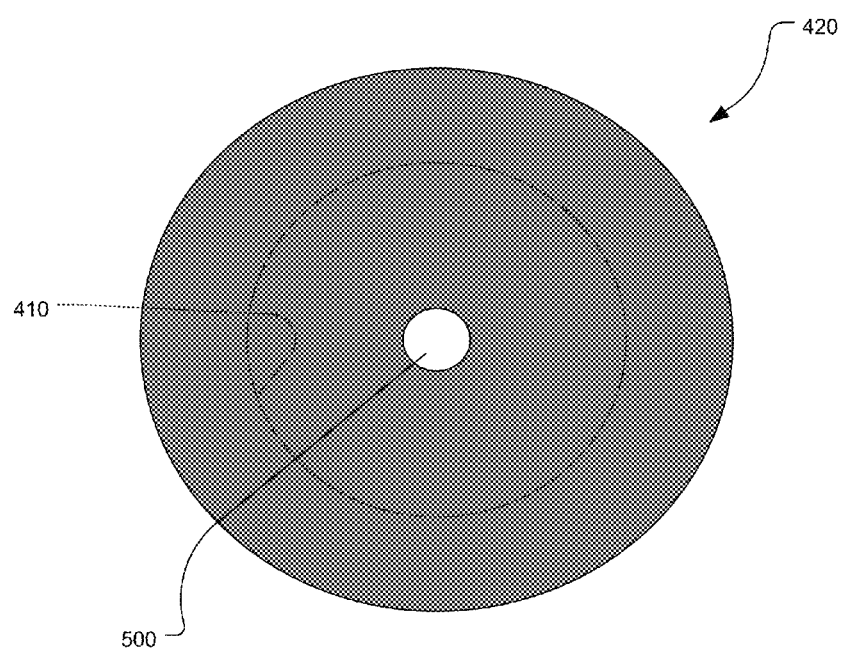
FIG. 5B is a top view of a membrane from the pressure sensor according to another embodiment of the invention.

FIGS. 5A-5B show two different types of membranes 420 extending over the port 410 of the substrate 400.

In FIG. 5A, the membrane 420 has a mirror coating 500 that covers the entire membrane 420. Alternatively, in FIG. 5B, the membrane 420 has a mirror coating 500 that covers only a center portion of the membrane 420.

Figure 6B:
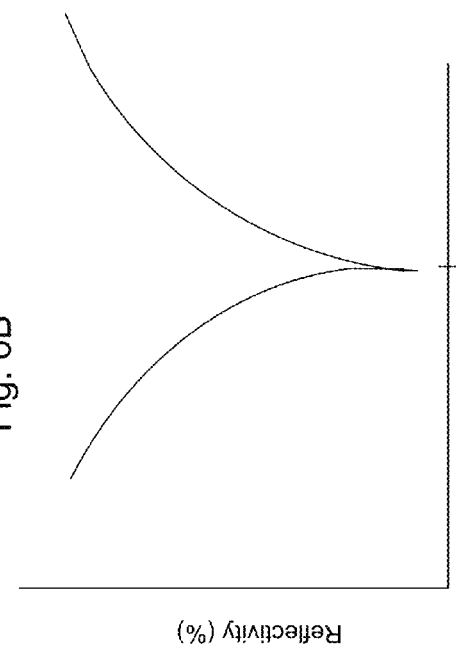
FIG. 6B is a plot of reflectivity as a function of wavelength (arbitrary units) for the pressure sensor illustrated in FIG. 6A.
Figure 6D:
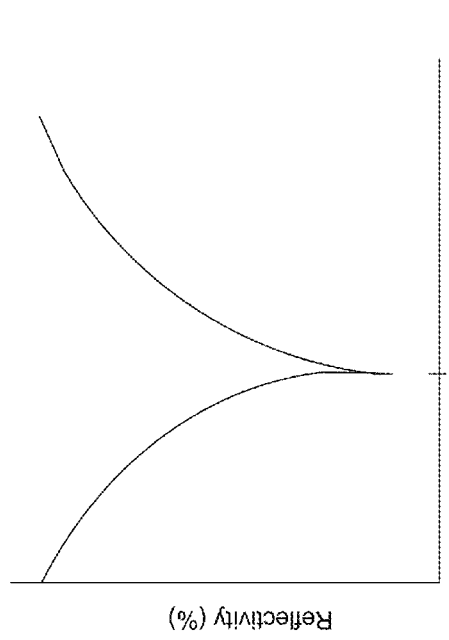
FIG. 6D is a plot of reflectivity as a function of wavelength (arbitrary units) for the pressure sensor illustrated in FIG. 6C.
Figure 6A:
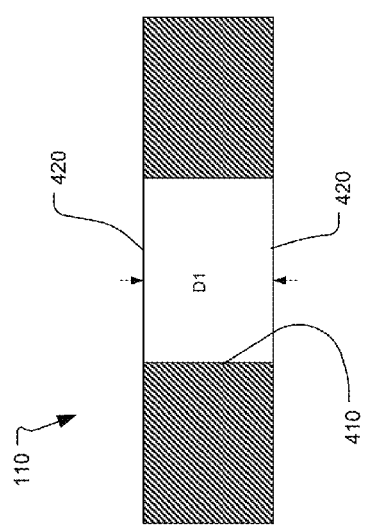
FIG. 6A is a schematic cross-sectional view of a pressure sensor in which the ambient pressure is equal to the pressure within the port.

FIG. 6A illustrates the mechanical response of the pressure sensor 110 when the ambient pressure is about equal to the internal manufacturing pressure within the port 410 of the sensor 110. Since these pressures are equal, the membranes 420 do not flex but maintain a level surface over the port 410. A distance D1 between the first membrane 420 and second membrane 420 can be determined and is associated with this particular ambient pressure.

FIG. 6B is a plot of reflectivity as a function of wavelength for the pressure sensor 110 in FIG. 6A. The membranes 420 function as an etalon or Fabry-Perot filter. When the swept source catheter 50 optically interrogates and scans the sensor 110, it acquires reflectivity (%) of the membranes 420 over a range of wavelengths ($\lambda$). Alternatively, the reflectivity is measured by another spectroscopy system including a broadband source and a spectrally resolved detector. The membranes 420 have a minimum reflectivity and maximum transmissivity at wavelength $\lambda 1$. This minimum reflectivity is based on the distance between the two membranes 420. Thus, distance D1 correlates with wavelength $\lambda 1$.

Figure 6C:
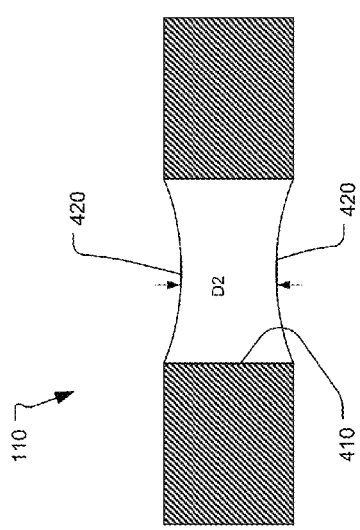
FIG. 6C is schematic cross-sectional view of the pressure sensor when the ambient pressure is greater than the pressure within the port.

FIG. 6C illustrates the mechanical response of the pressure sensor 110 when the ambient pressure is greater than the internal manufacturing pressure within the port 410 of the sensor 110. At this pressure difference, the membranes 420 flex inwards into the port 410. A distance D2 between the first membrane 420 and second membrane 420 can be determined and is associated with this particular ambient pressure.

FIG. 6D is a plot of reflectivity as a function of wavelength for the pressure sensor 110 in FIG. 6C. In this example, the membranes 420 have a minimum reflectivity and maximum transmissivity at wavelength $\lambda 2$ from data acquired by the swept source catheter 50. This minimum reflectivity is based on the distance D2 between the flexed membranes 420. Thus, distance D2 correlates with wavelength $\lambda 2$ When comparing the plots in FIGS. 6B and 6D, the reflection minimum wavelength $\lambda 2$ for the increased pressure shifted to the longer wavelengths compared with the equalized pressure reflection minimum wavelength $\lambda 1$. This shift is used to determine associated pressure being applied.

Figure 7:
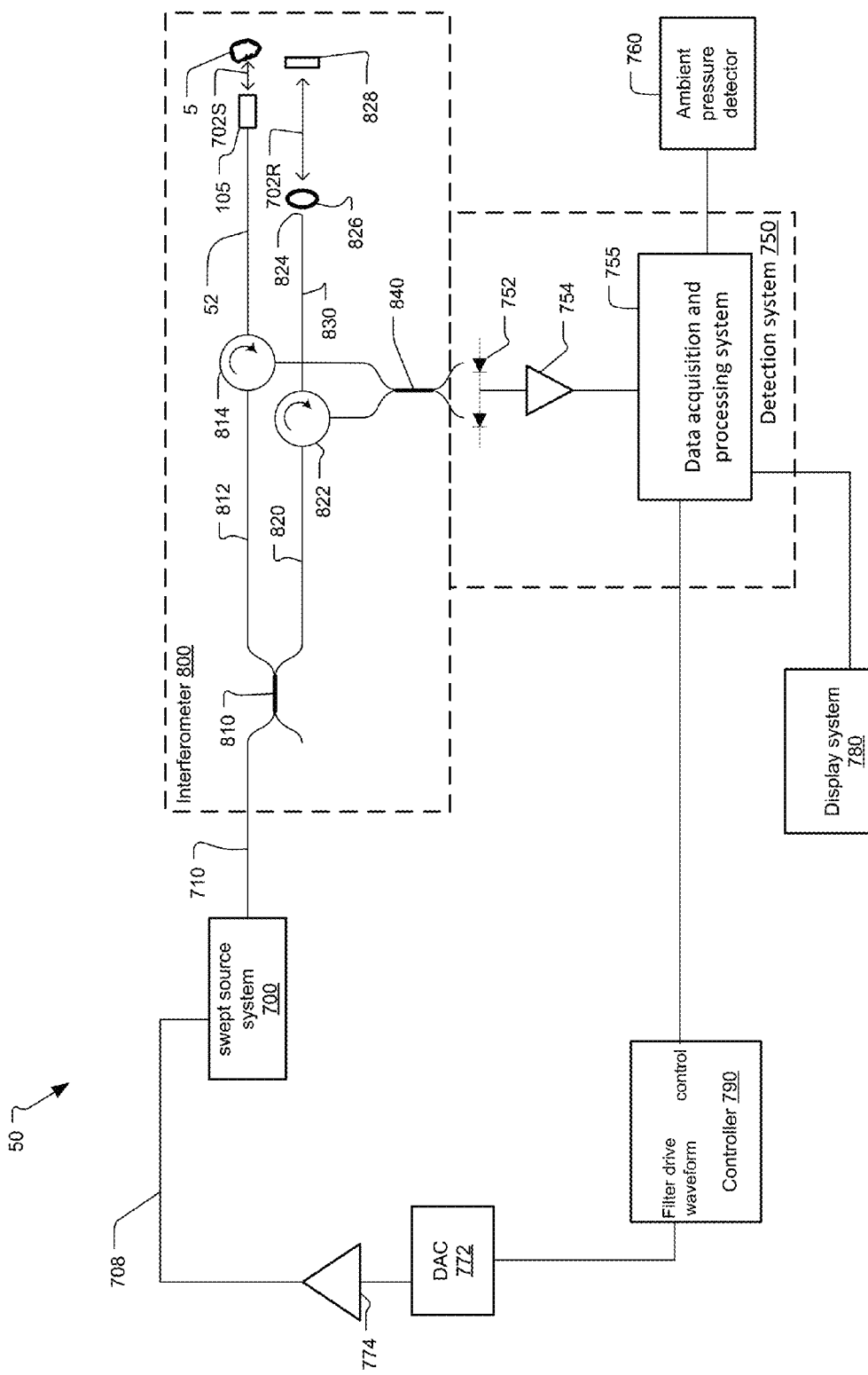
FIG. 7 is a schematic view of a swept source system according to an embodiment of the invention.

FIG. 7 shows one example of the components within a swept source catheter 50. In this example, the swept source catheter 50 is an optical coherence analysis system.

This embodiment includes the capability of performing spectroscopic and OCT analysis on a sample 5 such as the wall of the lumen/vessel 10. This embodiment also includes the capability of optically interrogating pressure sensors 110.

An optical swept source system 700 generates a tunable or swept optical signal on optical fiber 710 that is transmitted to interferometer 800. The swept optical signal scans over a scan band with a narrowband emission.

The swept source system 700 is generally intended for high speed tuning to generate swept optical signals that repeatedly scan over the scan band(s) at rates of greater than 1 kiloHertz (kHz). In current embodiments, the multi-sweep rate swept source system 700 tunes at speeds greater than 20 or 100 kHz. In very high speed embodiments, the multi-sweep rate swept source system 700 tunes at speeds greater than 200 or 500 kHz.

Typically, the width of the tuning or scan band is greater than 10 nanometers (nm). In the current embodiments, it is preferably between 50 and 150 nm, although even wider tuning bands are contemplated in some examples. On the other hand, the bandwidth of the narrowband emission has a full width half maximum (FWHM) bandwidth of less than 20 or 10 GigaHertz (GHz), and is usually 5 GHz or less. For optical coherence tomography, this high spectral resolution implies a long coherence length and therefore enables imaging deeper into samples, for example deeper than 5 millimeters (mm). On the other hand, in lower performance applications, for example OCT imaging less than 1 mm deep into samples, broader FWHM passbands are sometimes appropriate, such as passbands of about 200 GHz or less.

In one example, the swept source system 700 includes a tunable laser for generating the swept optical signals. The advantages of tunable lasers include high spectral brightness and relatively simple optical designs. A tunable laser is constructed from a gain medium, such as a semiconductor optical amplifier (SOA) that is located within a resonant cavity, and a tunable element such as a rotating grating, grating with a rotating mirror, or a Fabry-Perot tunable filter. Currently, some of the highest tuning speed/sweep rate lasers are based on the laser designs described in U.S. Pat. No. 7,415,049 B1, entitled Laser with Tilted Multi Spatial Mode Resonator Tuning Element, by D. Flanders, M. Kuznetsov and W. Atia, which is incorporated herein by this reference in its entirety. The use of micro-electro-mechanical system (MEMS) Fabry-Perot tunable filters combines the capability for wide spectral scan bands with the low mass, high mechanical resonant frequency deflectable MEMS membranes that have the capacity for high speed tuning/sweep rates. Another laser architecture is termed a Fourier-domain mode-locked laser (FDML). This type of laser stores light in a long length of fiber for amplification and recirculation in synchronism with the laser's tuning element. See "Fourier Domain Mode Locking (FDML): A new laser operating regime and applications for optical coherence tomography", R. Huber, M. Wojtkowski, and J. G. Fujimoto, 17 Apr. 2006/Vol. 14, No. 8/OPTICS EXPRESS 3225. The drawback of these devices is their complexity, however. Moreover, the ring cavity including the long storage fiber creates its own performance problems such as dispersion and instability.

Another class of swept sources that has the potential to avoid inherent drawbacks of tunable lasers is filtered amplified spontaneous emission (ASE) sources that combine a broadband light source, typically a source that generates light by ASE, with tunable filters and amplifiers. Some of the highest speed devices based on filtered ASE sources are described in U.S. Pat. No. 7,061,618 B2, entitled Integrated Spectroscopy System, by W. Atia, D. Flanders P. Kotidis, and M. Kuznetsov. A number of variants of the filtered ASE swept source are described, including amplified versions and versions with tracking filters. Still other configurations of the filtered ASE sources are described in U.S. patent application Ser. No. 12/553,295, filed on Sep. 3, 2009, entitled Filtered ASE Swept Source for OCT Medical Imaging, by D. Flanders, W. Atia, and M. Kuznetsov (U.S. Pat. Pub. No. US 2011/0051148 A1), which is incorporated herein in its entirety by this reference. This lays out various integrated, high speed filtered ASE swept source configurations. U.S. patent application Ser. No. 12/776,373, filed on May 8, 2010, entitled ASE Swept Source with Self-Tracking Filter for OCT Medical Imaging, by the same inventors (U.S. Pat. Pub. No. US 2011/0051143 A1), outlines still further configurations that rely on the use of a self-tracking filter arrangement that can improve performance both in terms of sweep rate and linewidth, among other things, and which is also incorporated herein in its entirety by this reference.

A controller 790 generates a drive waveform that is supplied to a digital to analog converter 772 (DAC). This generates a tunable element drive signal 708 that is amplified by amplifier 774 and applied to the swept source system 700. In one example, the controller 790 stores a filter drive waveform that linearizes the frequency sweep for one or more tunable optical filters, such as Fabry-Perot tunable filters or other tunable optical elements, contained in the swept source system 700.

In the example, a Mach-Zehnder-type interferometer 800 is used to analyze the optical signals from the sample 5. The swept optical signal from the swept source system 700 is transmitted on fiber 710 to a 90/10 optical fiber coupler 810 or other beam splitter, to give specific examples. The swept optical signal is divided between a reference arm 820 and a sample arm 812 of the system.

The optical fiber 830 of the reference arm 820 terminates at the fiber endface 824. The light 702R exiting from the reference arm fiber endface 824 is collimated by a lens 826 and then reflected by a mirror 828 to return back, in some exemplary implementations.

The external mirror 828 has an adjustable fiber to mirror distance, in one example. This distance determines the depth range being imaged, i.e. the position in the sample 5 of the zero path length difference between the reference arm 820 and the sample arm 812. The distance is adjusted for different sampling probes and/or imaged samples. Light 702R returning from the reference mirror 828 is returned to a reference arm circulator 822 and directed to a 50/50 fiber coupler 840. In other examples, such as those using free space optical configurations, the coupler 840 is often replaced with a partially reflecting mirror/beam splitter.

The fiber 52 on the sample arm 812 terminates at the sample arm probe 105. The exiting swept optical signal 702S is focused by the probe 105 onto the sample 5. Light returning from the sample 5 is returned to a sample arm circulator 814 and directed to the fiber coupler 840.

The reference arm signal and the sample arm signal are combined or mixed in the fiber coupler 840 or other beam combiner to generate an interference signal.

The interference signal is detected by a detection system 750. Specifically, a balanced receiver, comprising two detectors 752, is located at each of the outputs of the fiber coupler 840 in the illustrated embodiment. The electronic interference signal from the balanced receiver 752 is amplified by amplifier 754.

Once a complete data set has been collected of the sample 5 by spatially raster scanning the focused probe beam point over the sample, in a Cartesian geometry, x-y, fashion or a cylindrical geometry theta-z fashion, and the spectral response at each one of these points is generated from the frequency tuning of the optical swept source system 700, the data acquisition and processing system 755 performs a Fourier transform on the data in order to reconstruct the image and perform a 2D or 3D tomographic reconstruction of the sample 5. This information is displayed by the display system 780.

In one application, the probe 105 is inserted into blood vessels and used to scan the inner wall of arteries and veins. In other examples, other analysis modalities are included in the probe such as intravascular ultrasound (IVUS), forward looking IVUS (FLIVUS), high-intensity focused ultrasound (HIFU), pressure sensing wires and image guided therapeutic devices. In still other applications, the probe is used to scan different portions of an eye or tooth or other structure of a patient or animal. Such diagnostic imaging can also be used for image guided therapy and combined with therapeutic modalities, such as laser surgery.

The probe 105 is also used to determine the spectral response of the pressure sensors 110 during scanning and specifically determine the reflectivity minimums described in FIGS. 6B and 6D. In operation, the probe 105 scans the pressure sensors 110 while sweeping across a range of wavelengths. During this scanning and sweeping, the light returning from each pressure sensor 110 is returned to the sample arm circulator 814 and directed to the fiber coupler 840. From the fiber coupler 840, the signal is detected by the detection system 750 as described above.

The controller 790 monitors the response of the detectors 752. Based on this detection, the controller 790 determines the wavelength having the minimum reflectivity or maximum transmissivity. The controller 790 associates this minimum reflectivity with a specific pressure value. Thus, the pressure profile along the length of the sheath 20 can be determined based on the acquired spectral response, having the lowest reflectivity, for each pressure sensor.

The optical coherence analysis system of the swept source catheter 50 also includes an ambient pressure detector 760. The ambient pressure detector 760 measures the current ambient pressure for a location where the swept source catheter 50 is being used. For example, the ambient pressure is the pressure within a doctor's office or hospital room. This measured ambient pressure is inputted into the detection system 750 where it is directed to the controller 790. The controller 790 uses this detected ambient pressure as a base line for determining the pressure at each pressure sensor 110.

It should be noted that in the preferred embodiment, the spectral response is obtained by spectrally scanning the narrowband emission of the swept source 700 and then resolving the spectral response from the response of the detectors 752, over the period of the sweep. In an alternative configuration, the swept source 700 is replaced with a broadband source that emits a broadband signal that covers the scanband. The detectors 752 are then replaced with spectrally resolving detector systems. An example of such a detector system is described in U.S. Pat. No. 6,665,458. Another example uses a grating to spatially disperse the spectrum along with a linear detector array.

Figure 8A:
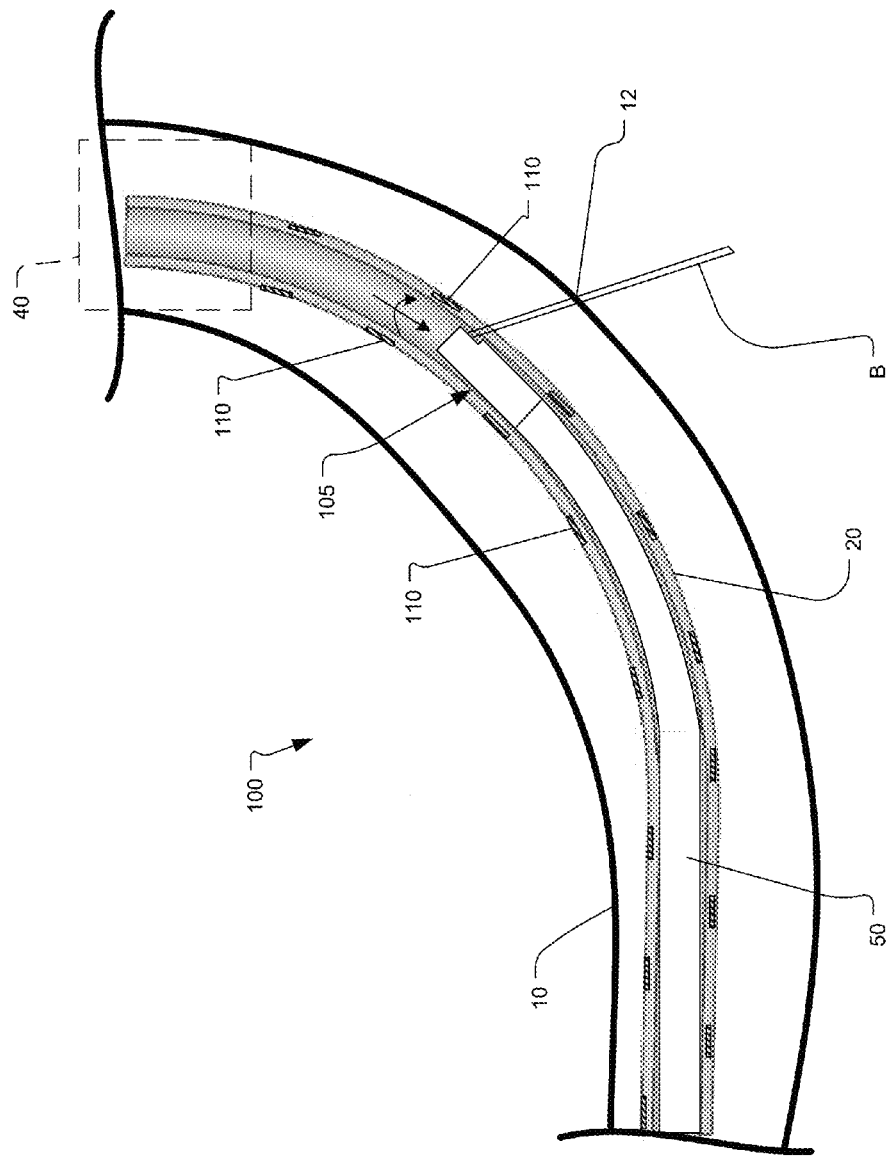
FIGS. 8A-8B are cross-sectional views of the intravascular pressure sensor system in operation showing the movement of the swept source catheter through the sheath.
Figure 8B:
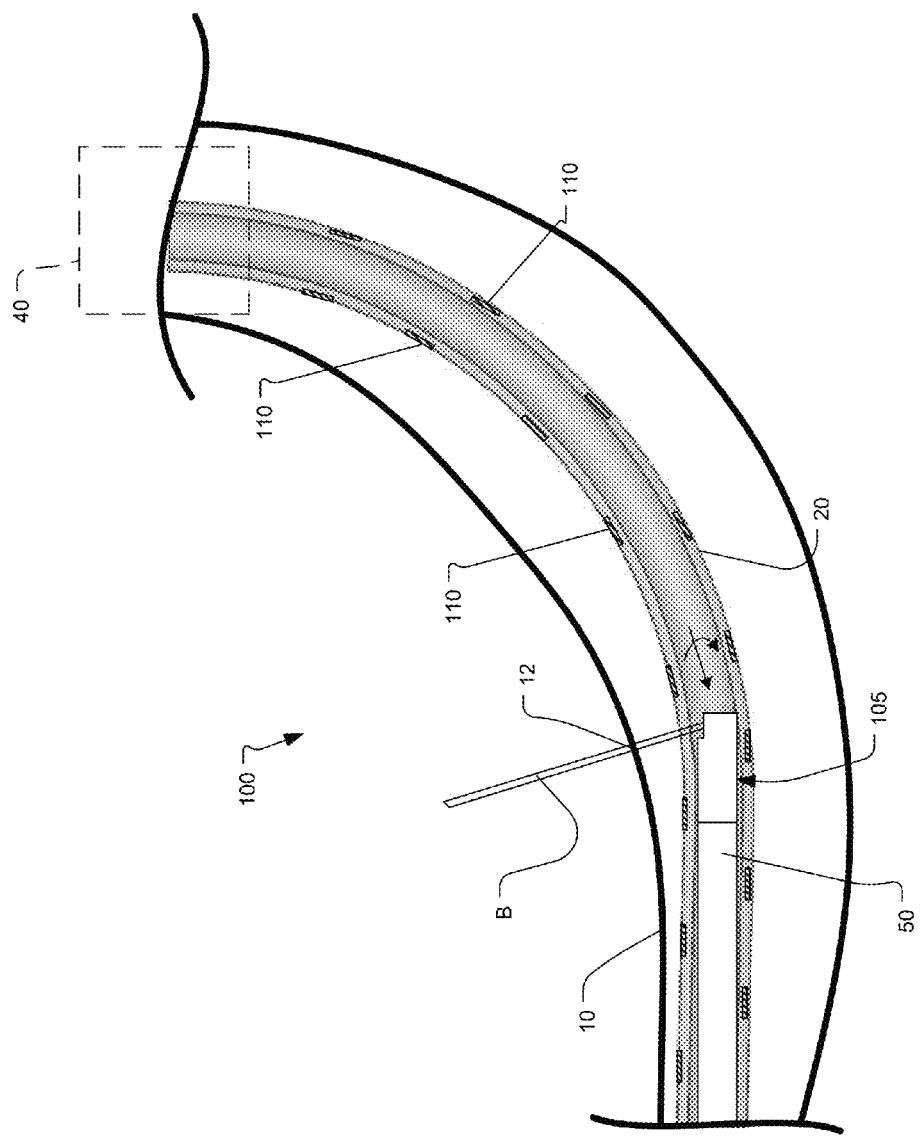

FIGS. 8A-8B show the movement of the swept source catheter 50 through the sheath 20 embedded with pressure sensors 110. As shown, the swept source catheter 50 scans the vessel 10 and pressure sensors 110 while being withdrawn from the sheath 20. The swept source catheter 50 is rotated during this scanning/withdrawing process.

Figure 9:
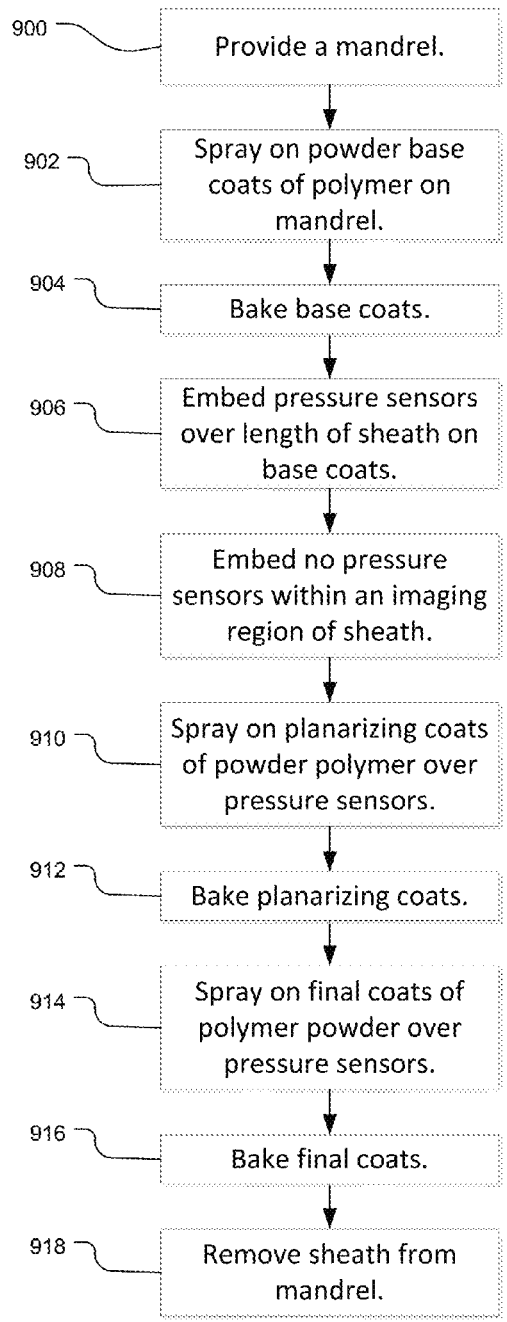
FIG. 9 is a flowchart illustrating a process of manufacturing pressure sensors in a sheath according to an embodiment of the invention.

FIG. 9 illustrates the process of manufacturing a sheath 20 embedded with pressure sensors 110.

This process includes a step 900 of providing a mandrel such as a core mandrel. Then, step 902 includes spraying on powder base coats of polymer onto the mandrel. In another example, a liner is placed over the mandrel before step 902.

The mandrel can be grounded and the powder charged as the unmelted powders are applied, thereby causing powders to electrostatically cling to the heated mandrel or liner during application. When this base polymer is sprayed onto the heated mandrel or liner, the powder melts to form a uniform coating over the surface.

The spraying technique is accomplished with spray heads that traverse the mandrel while the mandrel is being rotated. These spray heads apply atomized sprays of powder that fuse to the surface of the mandrel. Each spray head is connected to multiple containers of polymer materials and preferably an opacifier material, such as tungsten.

The coats of polymer are further baked in step 904. Baking occurs in an oven to consolidate the material within these base coats of polymer. More importantly, the baking ensures complete fusion of the sprayed polymer to the mandrel. The baking or heating can be accomplished with infrared, hot air, or resistance heating of the mandrel core.

Next, pressure sensors 110 are embedded over the length of the sheath 20 on the base coats in step 908. Step 910 includes spraying on planarizing coats of powder polymer over the pressure sensors 110. These planarizing coats are baked in step 912.

In step 914, final coats of polymer powder are sprayed over the pressure sensors 110. These final coats are baked in step 916.

In step 918, a sheath 20, embedded with pressure sensors 110, is removed from the mandrel.

Figure 10:
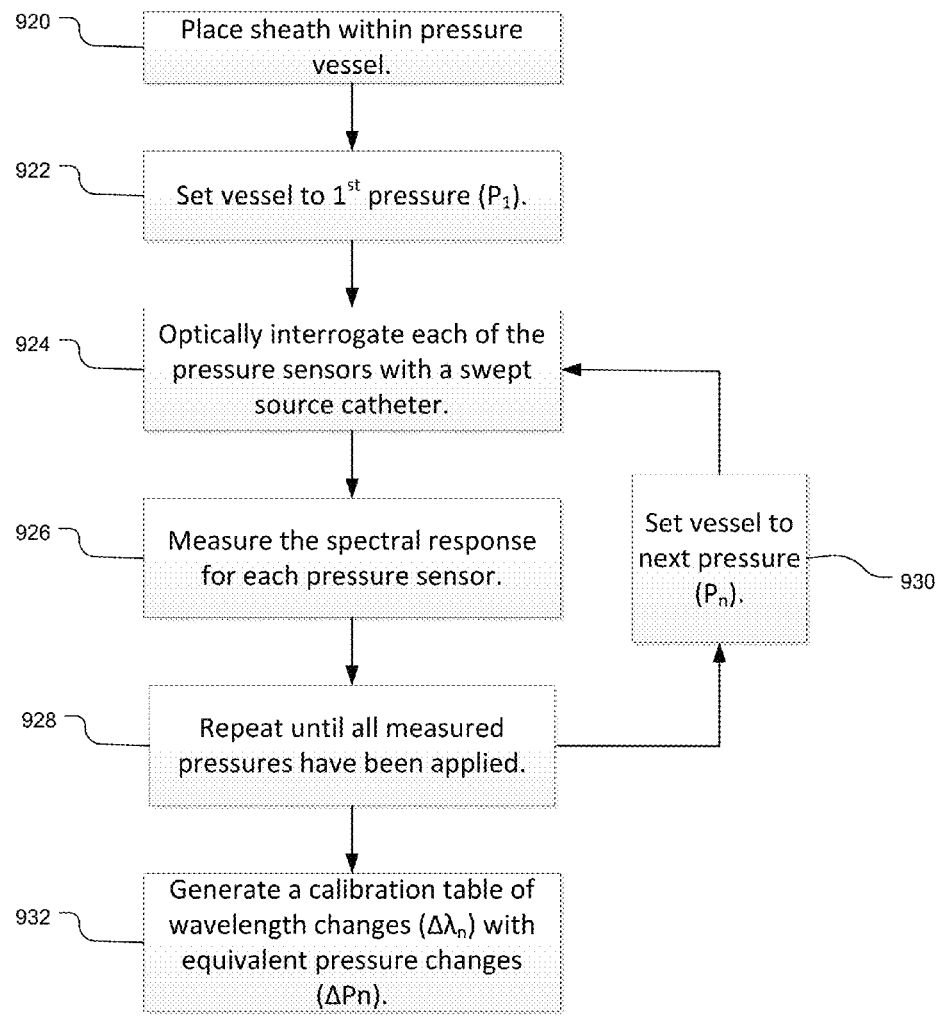
FIG. 10 is a flowchart illustrating a calibration of pressure sensors based on pressure measurements according to an embodiment of the invention.

FIG. 10 illustrates the process of calibrating pressure sensors 110 based on pressure measurements according to one example.

Initially in step 920, the embedded sheath 20 is placed within a pressure vessel. Next, in step 922, the vessel is set to a first pressure ($P_1$). Preferably the temperature is set to that of the human body.

In step 924, each of the pressure sensors 110 are optically interrogated with a swept source or broadband source with a spectrally resolving detector. The controller 790 in combination with the detection system 750 measures the spectral response for each pressure sensor 110 in step 926.

In step 928, steps 924 and 926 are repeated until all the measured pressures have been applied. Step 930 sets the vessel to a next pressure ($P_n$) as part of the repeating step 928.

In step 932, a calibration table is generated including wavelength changes ($\Delta\lambda_n$) corresponding with equivalent pressure changes ($\Delta P_n$). This calibration table is used by the controller 790 to determine the intravascular pressure along the lumen/vessel 10 during an operation in the patient.

Figure 11:
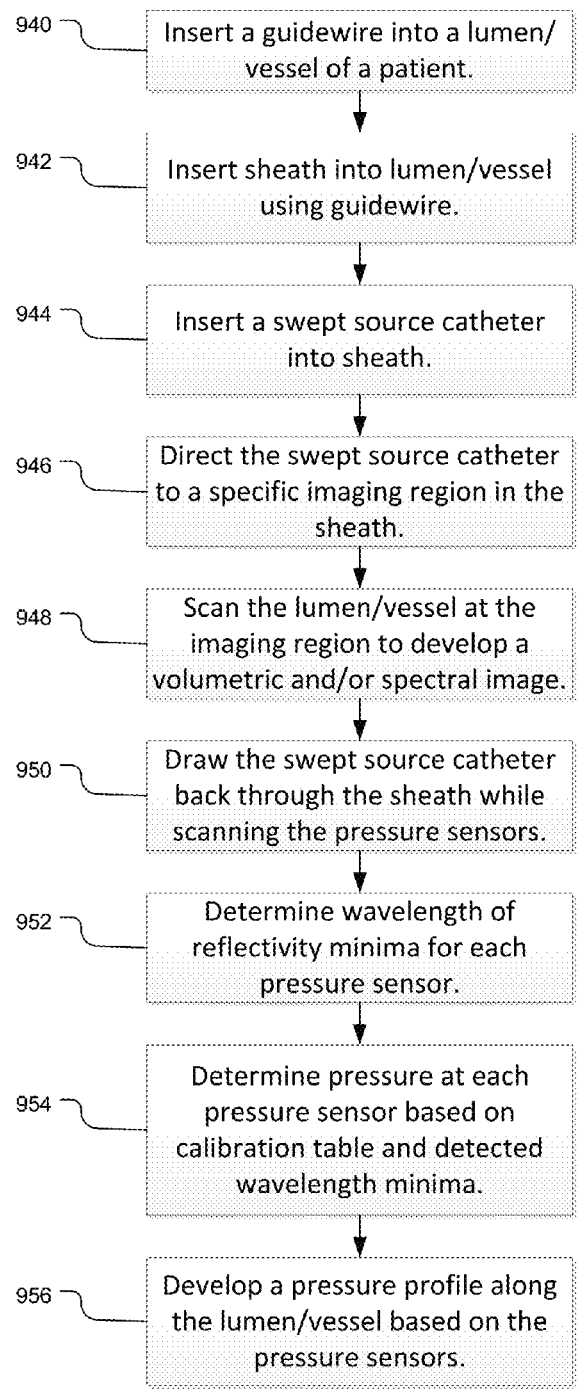
FIG. 11 is a flowchart illustrating a method of using pressure sensors with a swept source catheter according to an embodiment of the invention.

FIG. 11 is a method of using pressure sensors with a swept source catheter.

Initially in step 940, a guidewire is inserted into the lumen/vessel 10 of a patient. In step 942, the embedded sheath 20 is inserted into the lumen/vessel 10 using the guide wire. Then, in step 944, the swept source catheter 50 is inserted into the sheath 20.

In step 946, the swept source catheter 50 is directed to a specific imaging region 40 in the sheath 20. The swept source catheter 50 scans the lumen/vessel 10 at the imaging region 40 to develop a volumetric and/or spectral image in step 948. Then, the swept source catheter 50 is drawn back through the sheath 20 while scanning the pressure sensors 110 in step 950.

In step 952, the controller 790 within the swept source catheter 50 determines the wavelength of the reflectivity minima for each pressure sensor 110. Then, in step 954, the controller 790 determines a pressure at each pressure sensor 110 based on the calibration table, from step 932, and the detected wavelength minima, from step 952.

In step 956, the controller 790 develops a pressure profile along the lumen/vessel 10 based on the pressure sensors 110. It should also be appreciated that the pressure profile is also calibrated across temperature. As result, when multiple pressure sensors 110 are exposed to the same pressure then differences between those pressure sensors will be indicative of a temperature at the location of those sensors. In this way, the pressure sensors can also function as temperature sensors especially in the situation where the pressure sensors are located with a relatively high density along the length of the sheath 20.

Figure 12:
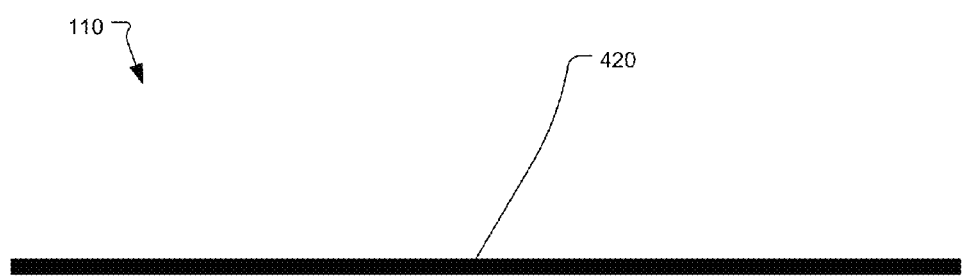
FIG. 12 is a cross-sectional view of the temperature sensor according to an embodiment of the invention.

FIG. 12 illustrates still another embodiment of the sensor 110. In this example, the sensor 110 simply includes a single membrane 420. In one example, this membrane 420 is constructed from a thermochromic material or composite material. In other examples, the thermochromic material is applied to the substrate. Such materials change color in response to temperature. In one example, the thermochromic composite material is liquid crystal material. When these thermochromic sensors 110 are embedded in the sheath 20, and then scanned by the catheter 50, the temperature along the length of the sheath 20 is resolved to detect hotspots, for example, in the coronary arteries, for example.

While this invention has been particularly shown and described with references to preferred embodiments thereof, it will be understood by those skilled in the art that various changes in form and details may be made therein without departing from the scope of the invention encompassed by the appended claims.

What is claimed is:

1. An intravascular sensor system comprising:
   a sheath configured to be inserted into a vessel of a patient, the sheath including:
   an intravascular sensor array comprising a plurality of optical pressure sensors embedded within a wall of the sheath along a length of the sheath, and
   a lumen extending along the length of the sheath adjacent to the intravascular sensor array; and a catheter sized and shaped for selective insertion within the lumen of the sheath, the catheter including an optical fiber for transmitting an optical beam for optically interrogating individual optical pressure sensors of the plurality of optical pressure sensors as the catheter moves within the lumen along the length of the sheath.

2. The intravascular sensor system of claim 1, wherein each of the optical pressure sensors comprises:
a substrate having a central port;
a first membrane extending over one end of the central port; and
a second membrane extending over the other end of the central port.

3. The intravascular sensor system of claim 2, wherein the substrate is fabricated from wafer material.

4. The intravascular sensor system of claim 2, wherein each membrane includes a mirror coating on at least one face of the membrane.

5. The intravascular sensor system of claim 4, wherein the mirror coating completely covers the membrane.

6. The intravascular sensor system of claim 1, wherein the intravascular sensor array further comprises optical temperature sensors.

7. A method of detecting an intravascular pressure, comprising:
inserting into a vessel of a patent an intravascular sheath comprising a sensor array, the sensor array comprising a plurality of optical sensors embedded within a wall of the sheath and spaced along a length of the sheath;
inserting an optical catheter into a lumen of the sheath;
scanning the vessel with an optical signal from the catheter along the length of the sheath;
drawing the catheter through the lumen along the length of the sheath to interrogate individual optical sensors of the plurality of optical sensors along the length of the sheath; and
determining pressures and/or temperatures at the individual optical sensors based on optical responses of the individual optical sensors to the optical signal from the catheter.

8. The method of detecting in claim 7, further comprising using a guidewire to insert the intravascular sheath into the vessel.

9. A method of detecting an intravascular pressure, comprising:
inserting into a vessel of a patient an intravascular sheath comprising a sensor array, the sensor array comprising a plurality of sensors embedded within a wall of the intravascular sheath along a length of the intravascular sheath;
inserting an optical catheter into the intravascular sheath;
scanning the vessel with an optical signal from the catheter along the length of the intravascular sheath;
drawing the catheter through the intravascular sheath;
scanning individual sensors of the plurality of sensors with the optical signal;
determining pressures and/or temperatures at the individual sensors based on optical responses of the individual sensors to the optical signal; and
generating a volumetric image of the vessel using the optical signal.

10. The method of detecting in claim 7, wherein the scanning of the sensors further comprises determining a wavelength of reflectivity minima for each sensor.

11. The method of detecting in claim 7, further comprising developing a pressure and/or temperature profile along the vessel based on the scanning of the sensors.

12. The method of claim 9, wherein the volumetric image is generated based on the scan of the vessel with the optical signal.

13. The method of claim 9, wherein the drawing the catheter through the sheath and scanning the sensors is performed simultaneously.

14. The method of claim 13, wherein the catheter is rotated when being drawn through the sheath and scanning the sensors.

15. The method of claim 9, wherein the drawing the catheter through the sheath and scanning the vessel is performed simultaneously.

16. The method of claim 9, wherein the sensors are spaced along a length of the sheath and the drawing the catheter through the sheath includes drawing the catheter through a lumen of the sheath along the length of the sheath.

17. The method of claim 9, wherein the catheter is inserted into a central lumen of the sheath and the sensors are embedded within a wall of the sheath surrounding the central lumen.

* * * * *